(12) United States Patent
Stone

(10) Patent No.: US 8,491,609 B2
(45) Date of Patent: Jul. 23, 2013

(54) DEVICE FOR REPAIRING A MENISCAL TEAR

(75) Inventor: Kevin T. Stone, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/551,453

(22) Filed: Jul. 17, 2012

(65) Prior Publication Data
US 2013/0012962 A1    Jan. 10, 2013

Related U.S. Application Data

(62) Division of application No. 12/437,605, filed on May 8, 2009, now Pat. No. 8,241,305.

(60) Provisional application No. 61/051,520, filed on May 8, 2008.

(51) Int. Cl.
*A61B 17/04* (2006.01)
*A61B 17/12* (2006.01)

(52) U.S. Cl.
USPC .......................................................... 606/144

(58) Field of Classification Search
USPC .......................................... 606/139, 144–150
See application file for complete search history.

(56) References Cited

U.S. PATENT DOCUMENTS 5,817,112 A * 10/1998 Christoudias ................. 606/148
2005/0228407 A1 * 10/2005 Nobles et al. ................. 606/144

* cited by examiner

*Primary Examiner* — Melanie Tyson
(74) *Attorney, Agent, or Firm* — Harness, Dickey

(57) ABSTRACT

A device for implanting a suture including an elongated shaft that extends from the main body and has a distal end that includes a pointed tissue piercing tip. A first suture support is mounted to the distal end, and a second suture support may be included. The first suture support has a first opening and is movable between a retracted position where the first suture support does not extend from the distal end and an extended position where the first suture support does extend from the distal end. A first suture capturing device is mounted to the distal end and is aligned with the first suture support. The first suture capturing device is movable between a retracted position in which it does not extend from the distal end and an extended position in which it does extend from the distal end.

17 Claims, 15 Drawing Sheets

DEVICE FOR REPAIRING A MENISCAL TEAR

CROSS-REFERENCE TO RELATED APPLICATIONS

This application is a divisional of U.S. application Ser. No. 12/437,605 filed May 8, 2008 (issued as U.S. Pat. No. 8,241,305 on Aug. 14, 2012), which claims benefit of United States Provisional Application No. 61/051,520 filed on May 8, 2008. The entire disclosures of the above applications are incorporated herein by reference.

FIELD

The present disclosure relates to medical devices and methods of use. In particular, the present disclosure relates to devices for repairing meniscal tears and methods of using the devices.

BACKGROUND

The statements in this section merely provide background information related to the present disclosure and may not constitute prior art.

In humans, two menisci rest between the femur and the tibia. The menisci are made of tough cartilage and conform to the surfaces of the bones upon which they rest. Due to traumatic injury or degenerative processes, the menisci may tear. Devices and methods are needed to repair such a tear.

SUMMARY

The present teachings provide for a device for implanting a suture. The device includes an elongated shaft that extends from the main body and has a distal end that includes a pointed tip. A first suture support is mounted to the distal end. The first suture support has a through hole and is movable between a retracted position where the first suture support does not extend from the distal end and an extended position where the first suture support does extend from the distal end. A first suture capturing device is mounted to the distal end and is aligned with the first suture support. The first suture capturing device is movable between a retracted position in which it does not extend from the distal end and an extended position in which it does extend from the distal end. The first suture capturing device extends within the through hole of the first suture support when in the extended position. The suture extends from the first suture support to the tip and extends into the main body through an opening in the tip.

The present teachings also provide for a method for repairing a meniscus having a tear. The method includes the following: mounting a suture to a suture implantation device having a pointed tip; inserting the suture implantation device into the meniscus and the tear such that a distal end of the device and at least a portion of the suture pass through the meniscus and the tear, the pointed tip forming a first hole through the meniscus and the tear; actuating a first button of the device to move a first suture support mounted to the distal end from a retracted position to an extended position in which the first suture support extends from the distal end, the suture positioned to extend across the first suture support to the tip; actuating a second button of the device to move a first suture capturing device from a retracted position to an extended position in which the first suture capturing device extends from the distal end to form a second hole through the meniscus and the tear and passes through an opening in the suture support; returning the first suture capturing device to the retracted position from the extended position, the suture being captured by the suture capturing device and pulled through the second hole formed in the tear by the suture capturing device as the suture capturing device returns to the retracted position; withdrawing the device from within the meniscus such that the distal end passes back through the first hole and the suture remains within the meniscus such that it extends across the tear and is threaded through the first hole and the second hole; and tightening the suture to close the tear and securing the suture in position.

The present teachings further provide for a method for repairing damaged tissue. The method includes the following: mounting a suture to a suture implantation device having a pointed tip; piercing a first hole in the tissue using the pointed tip by inserting the suture implantation device into the tissue such that a distal end of the device and at least a portion of the suture pass through the tissue; actuating a first button of the device to move a first suture support mounted to the distal end from a retraced position to an extended position in which the first suture support extends from the distal end, the suture positioned to extend across the first suture support to the tip; actuating a second button of the device to move a first suture capturing device from a retracted position to an extended position in which the first suture capturing device extends from the distal end to pierce a second hole in the tissue and passes through an opening in the suture support; returning the first suture capturing device to the retracted position from the extended position, the suture being captured by the suture capturing device and pulled through the second hole formed in the tissue by the suture capturing device as the suture capturing device returns to the retracted position; withdrawing the device from within the tissue such that the distal end passes back through the first hole and the suture remains within the tissue and is threaded through the first hole and the second hole; and tightening the suture to secure the suture into position.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
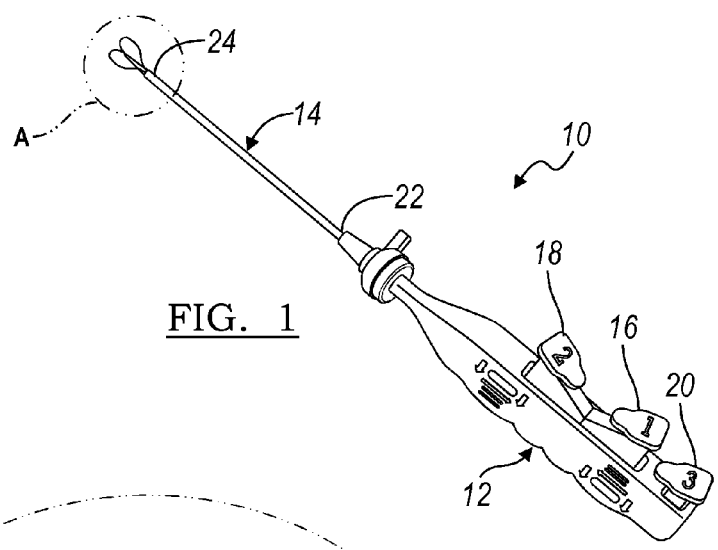
FIG. 1 is a perspective view of a device for repairing a meniscal tear according to the present teachings.

With initial reference to FIG. 1, a suture device according to the present teachings is illustrated at reference numeral 10. The device 10 includes a main body 12 and an extended or elongated shaft portion 14 that extends from the main body 12.

The main body 12 includes at least one button, switch, or any other device suitable for operating the device 10. As illustrated, the main body 12 includes a first button 16, a second button 18, and a third button 20. The device 10 can include any suitable number of buttons for operating or activating the device 10.

The extended shaft portion 14 includes a proximal end 22 and a distal end 24. The proximal end 22 is mounted to the main body 12. The distal end 24 is opposite to the proximal end 22.

Figure 1A:
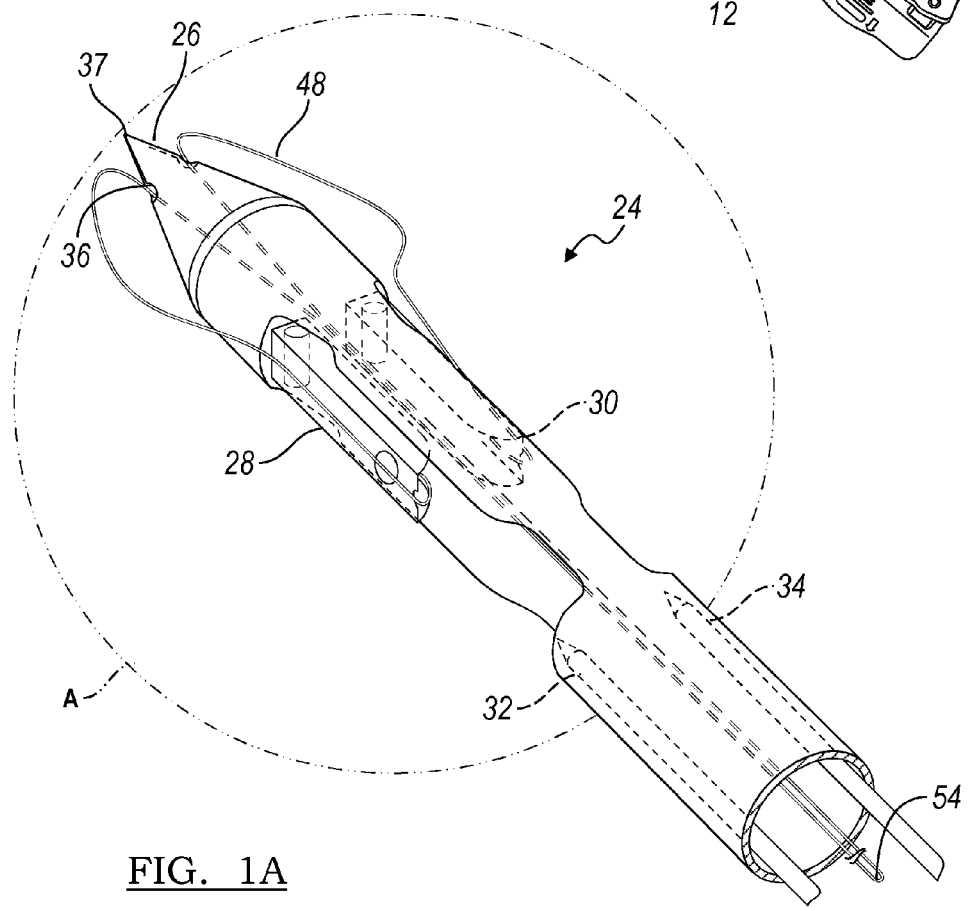
FIG. 1A is a perspective view of a distal end of the device of FIG. 1.

With additional reference to FIG. 1A, the distal end 24 includes a pointed conical tip 26, a first retractable wing 28, a second retractable wing 30, a first needle 32, and a second needle 34.

The pointed conical tip 26 is designed to pierce tissue, such as soft tissue, muscle, and bone. The pointed conical tip 26 can be sharpened to facilitate piercing the tissue. The pointed conical tip 26 includes or defines a pair of openings 36 connected by a slot 37. The openings 36 can be located at any suitable location on the tip 26. The slot 37 extends between the openings 36 across a distal portion of the tip 26.

Figure 2:
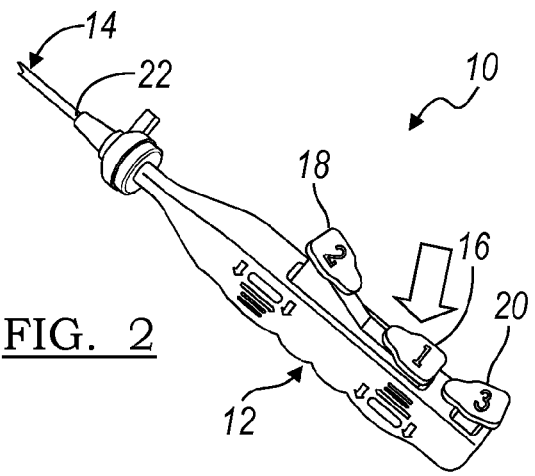
FIG. 2 is a perspective view of the device of FIG. 1 with a first button depressed.
Figure 2A:
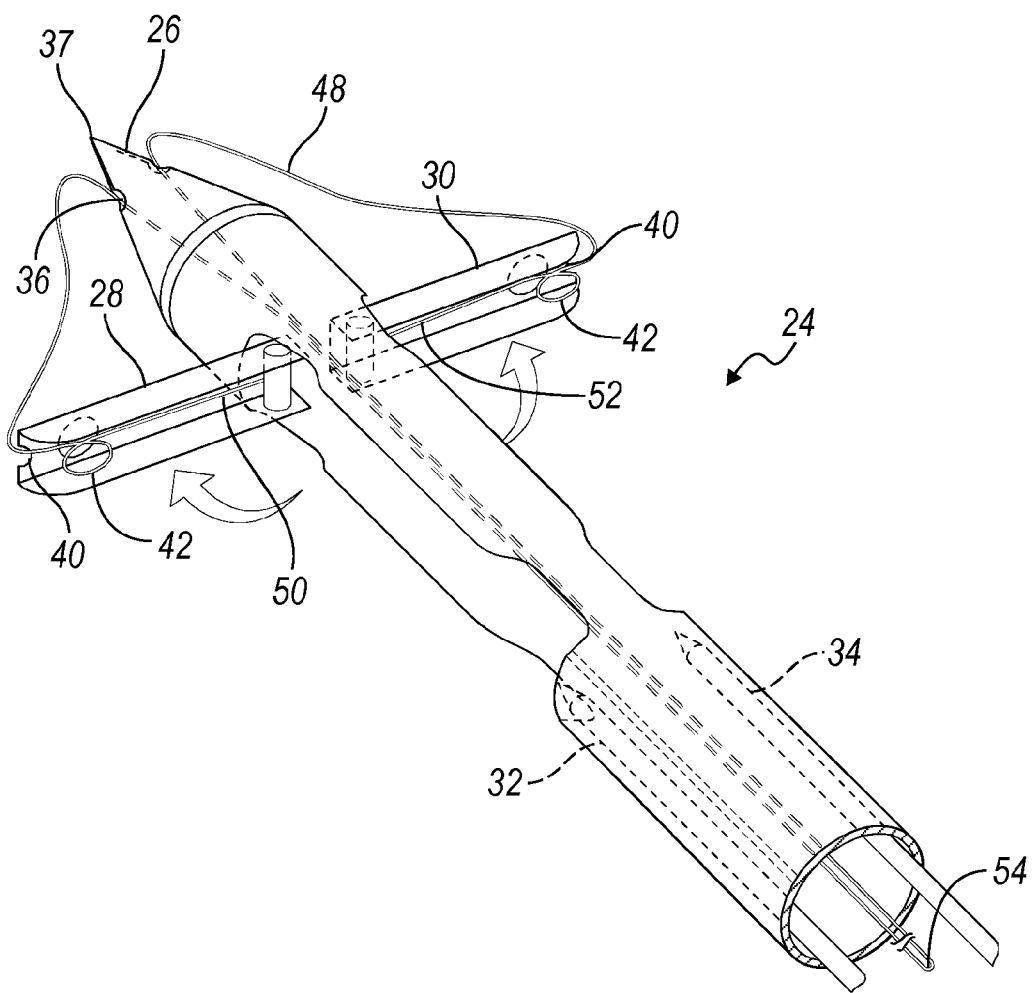
FIG. 2A is a perspective view of the distal end of the device of FIG. 1 with first and second wings illustrated in an extended position.

The first and the second retractable wings 28 and 30 are positioned at opposite sides of the distal end 24. The first and the second wings 28 and 30 can take the form of any device suitable for supporting a suture. As further illustrated in FIG. 2A, each of the first wing 28 and the second wing 30 include a suture guide 40 and a needle opening 42. The suture guides 40 can take the form of any suitable device for guiding a suture from the extended shaft portion 14 around the wings 28 and 30 and to the tip 26. For example, the suture guides 40 can take the form of recesses, indentations, or c-channels formed in the wings 28 and 30. The needle openings 42 are openings in each of the first wing 28 and the second wing 30 that extend completely through each of the first and second wings 28 and 30 and are each sized to receive one of the needles 32 and 34.

Each wing 28 and 30 is movable between a retracted position (FIG. 1A) in which the wings 28 and 30 do not extend from the distal end 24 and an extended position (FIG. 2A) in which the wings 28 and 30 do extend from the distal end 24. The wings 28 and 30 are movable to the extended position by actuating the first button 16 (FIG. 2) and are movable to the retracted position by actuating the third button 20 (FIG. 4), as further described herein.

Figure 3:
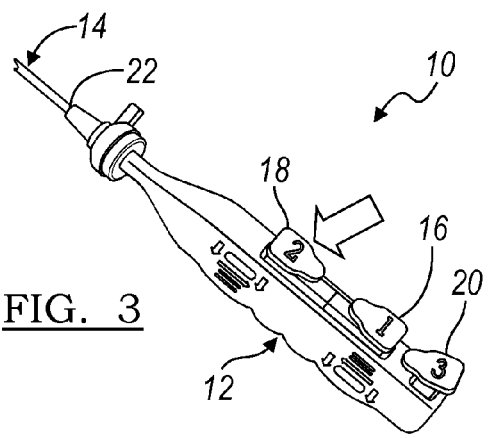
FIG. 3 is a perspective view of the device of FIG. 1 with a second button depressed.
Figure 3A:
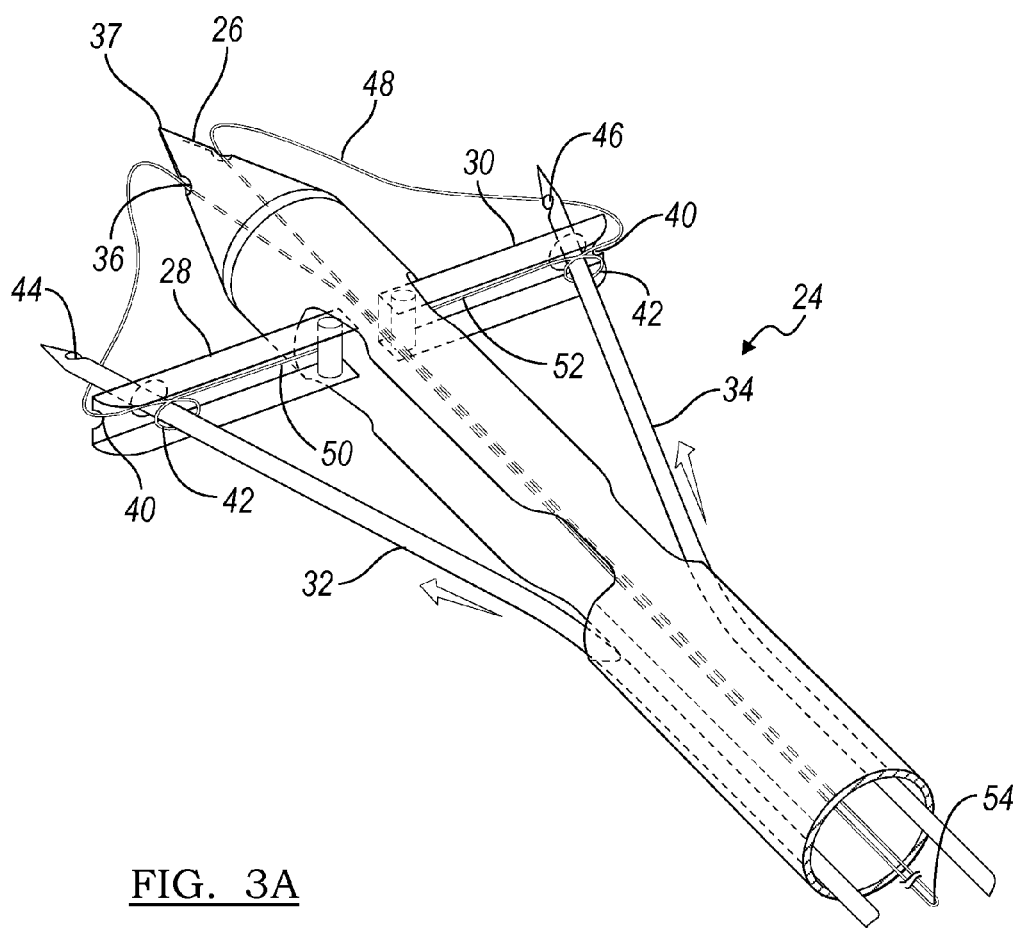
FIG. 3A is a perspective view of the distal end of the device of FIG. 1 with first and second needles illustrated in an extended position.

With additional reference to FIG. 3A, the first and second needles 32 and 34 can be any suitable device capable of penetrating biological matter, such as meniscal tissue, and capturing and/or retaining a suture. The first and second needles 32 and 34 can each include a retention surface or notch 44 and 46 respectively. The retention surfaces 44 and 46 can be any suitable surface or device for retaining and/or capturing a suture. For example, the retention surfaces 44 and 46 can be hooks or notches formed within each of the first needle 32 and the second needle 34 respectively.

The first and second needles 32 and 34 are positioned at opposite sides of the distal end 24. A position of the first needle 32 corresponds to a position of the first wing 28. A position of the second needle 34 corresponds to a position of the second wing 30.

Figure 4:
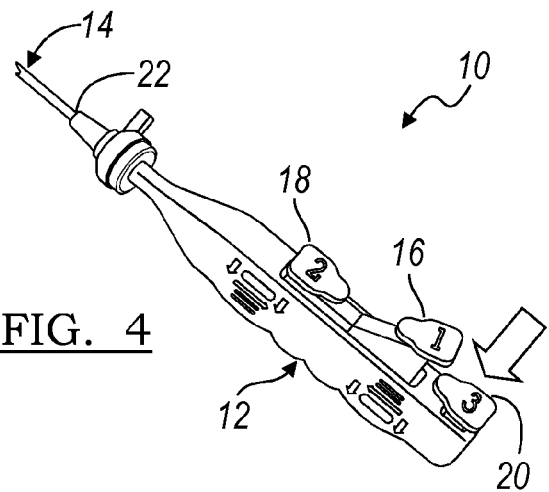
FIG. 4 is a perspective view of the device of FIG. 4 with a third button depressed.
Figure 4A:
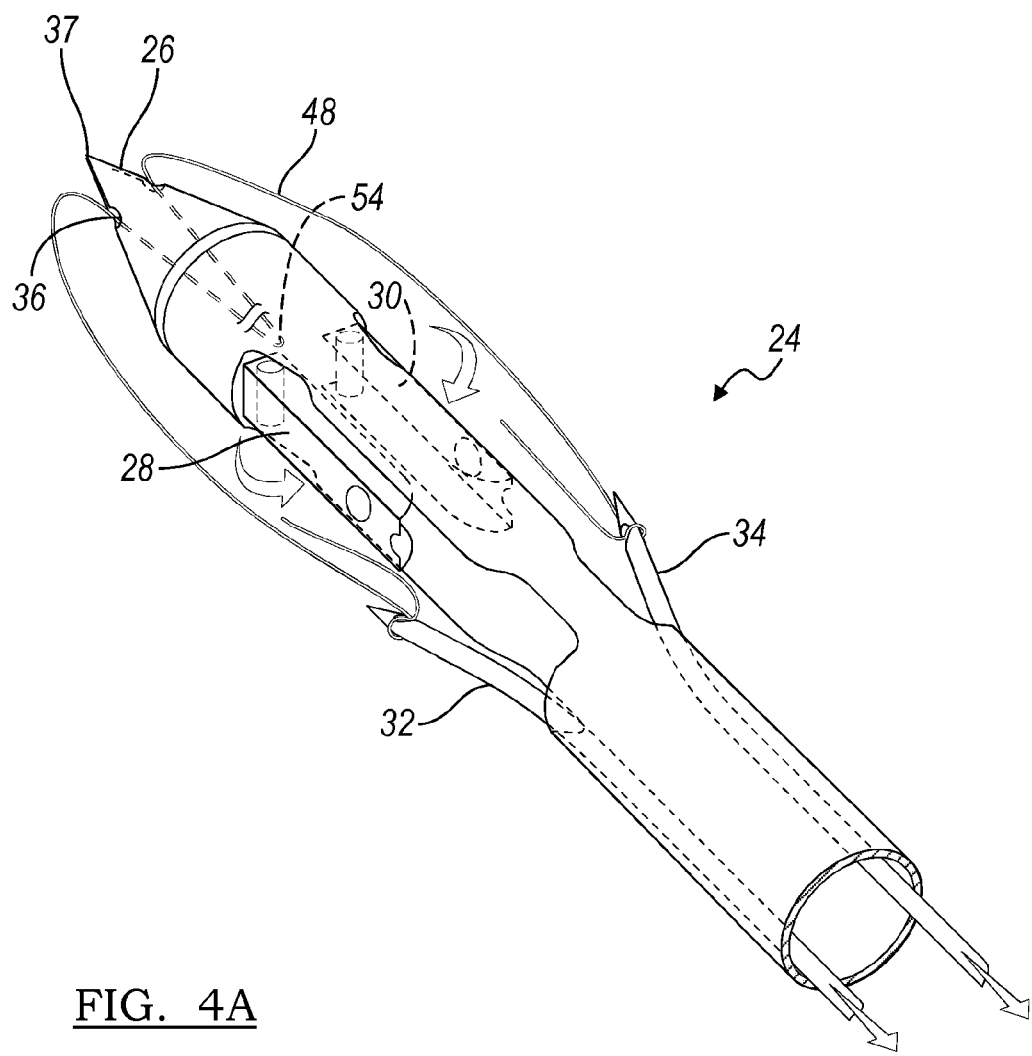
FIG. 4A is a perspective view of the distal end of the device of FIG. 1 with the first and the second wings illustrated in a retracted position and the first and the second needles in the process of moving from the extended position to a retracted position.

The first and the second needles 32 and 34 are movable between a retracted position (FIGS. 1A and 2A) and an extended position (FIG. 3A). In the retracted position, the first and second needles 32 and 34 do not protrude from the extended shaft portion 14. In the extended position, the first needle 32 extends through the needle opening 42 of the first wing 28 and the second needle 34 extends through the needle opening 42 of the second wing 30. The first and second needles 32 and 34 are prealigned with the needle openings 42 so that when the needles 32 and 34 are moved to the extended position the needles 32 and 34 extend through the openings 42. The first and second needles 32 and 34 can be moved from the retracted position to the extended position by pressing the second button 18 (FIG. 3). The needles 32 and 34 return to the retracted position after reaching the extended position, as illustrated in FIG. 4A. The needles 32 and 34 are returned to the retracted position using any suitable device, such as a spring mechanism.

The distal end 24 is configured to receive any suitable fastening device for use in repairing a menicsal tear. The fastening device is illustrated as a suture 48. When in use, the suture 48 is mounted to the distal end 24 such that a first end 50 of the suture 48 is mounted to, or proximate to, the first wing 28 and a second end 52 is mounted to, or proximate to, the second wing 30. From the first end 50, the suture 48 extends along the first wing 28 within the suture guide 40 to the tip 26, where the suture 48 passes through the opening 36 and into the distal end 24. The suture 48 extends within the distal end 24 and then returns back to the tip 26 at a loop 54. The suture 48 extends back through the opening 36 to the second wing 30. The suture 48 extends around the second wing 30 to the distal end 24 along the suture guide 40 of the second wing 30 and is secured at the distal end 24.

With reference to FIGS. 1-5, operation of the device 10 will now be described. With the suture 48 in position as described above and as illustrated in FIG. 1A, the first button 16 can be depressed (FIG. 2) to move the first wing 28 and the second wing 30 into the extended position of FIG. 2A. The second button 18 can be depressed (FIG. 3) to move the first and the second needles 32 and 34 to the extended position in which the needles 32 and 34 extend through the openings 42 in the first and the second wings 28 and 30.

Figure 5:
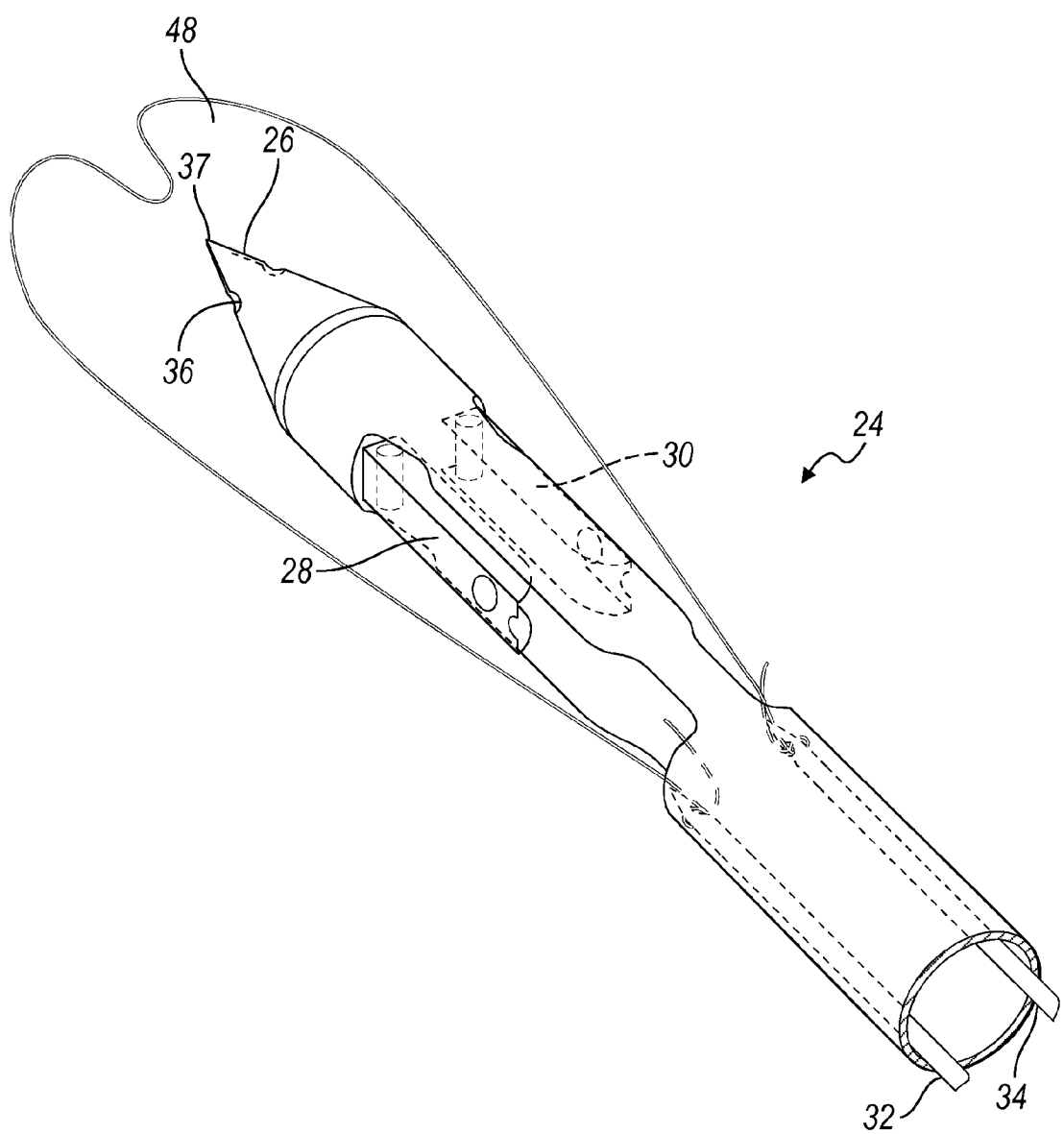
FIG. 5 is a perspective view of the distal end of the device of FIG. 1 with the first and the second needles illustrated in a further retracted position to withdraw a suture from the device.
Figure 6:
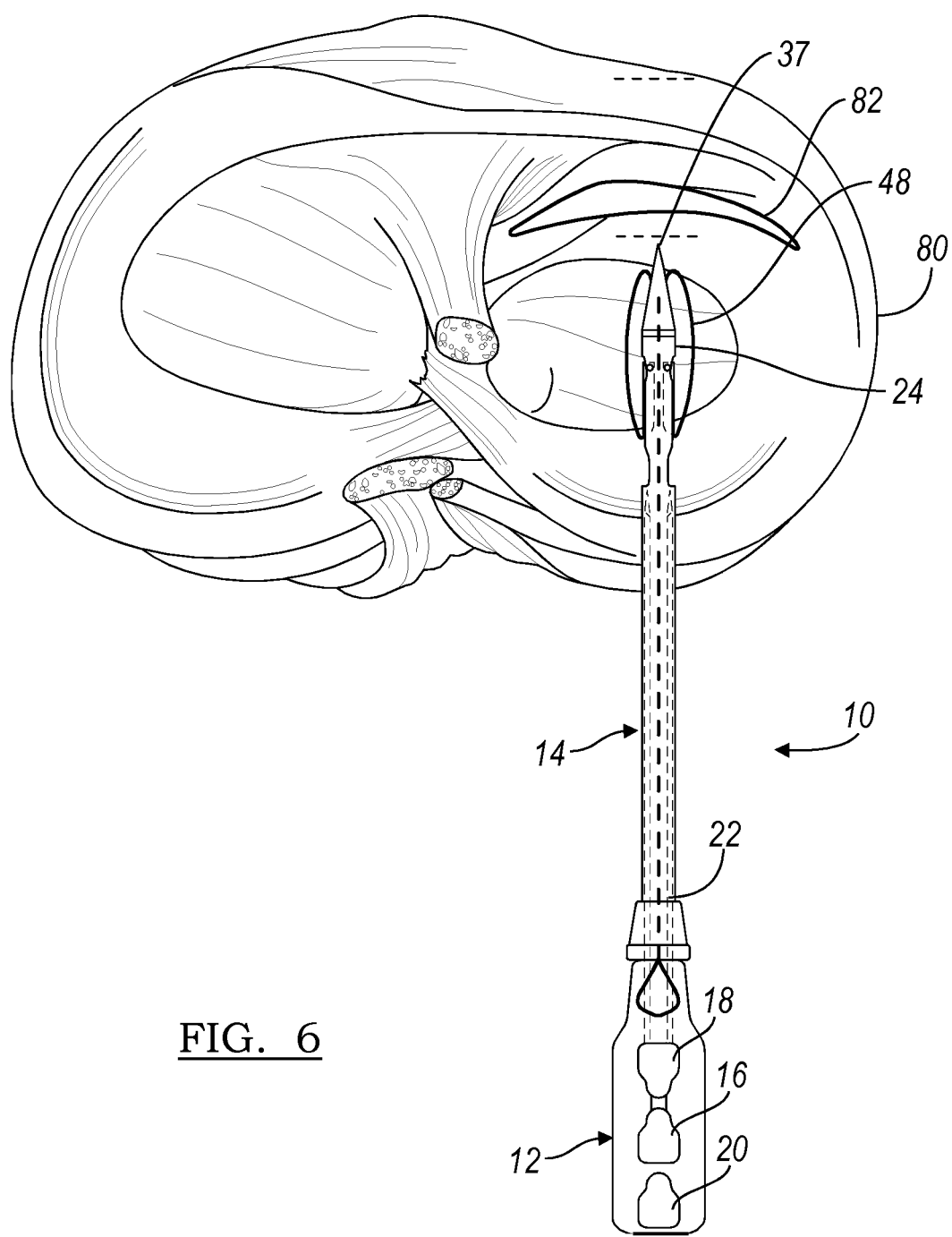
FIG. 6 is a top view of the device of FIG. 1 and a superior view of a meniscus having a tear to be sutured using the device.

From the extended position of FIG. 3A, the first and the second needles 32 and 34 revert to the retracted position. As the first and the second needles 32 and 34 retract, the suture 48 is captured by the retention surfaces 44 and 46 and the first and the second wings 28 and 30 can be moved back to the retracted position by pressing the third button 20, as illustrated in FIGS. 4 and 4A. As the first and the second needles 32 and 34 retract, they pull the suture 48 such that the loop 54 extends out from within the distal end 24, as illustrated in FIG. 5.

With additional reference to FIGS. 6-12, use of the device 10 to repair a meniscus 80 having a tear 82 is illustrated. To close the tear 82, the suture 48 is attached to the distal end 24 of the device 10 and the distal end 24 is inserted through the meniscus 80 and through the tear 82. The tissue piercing pointed tip 26 facilitates insertion of the device 10 through the meniscus 80.

Figure 7:
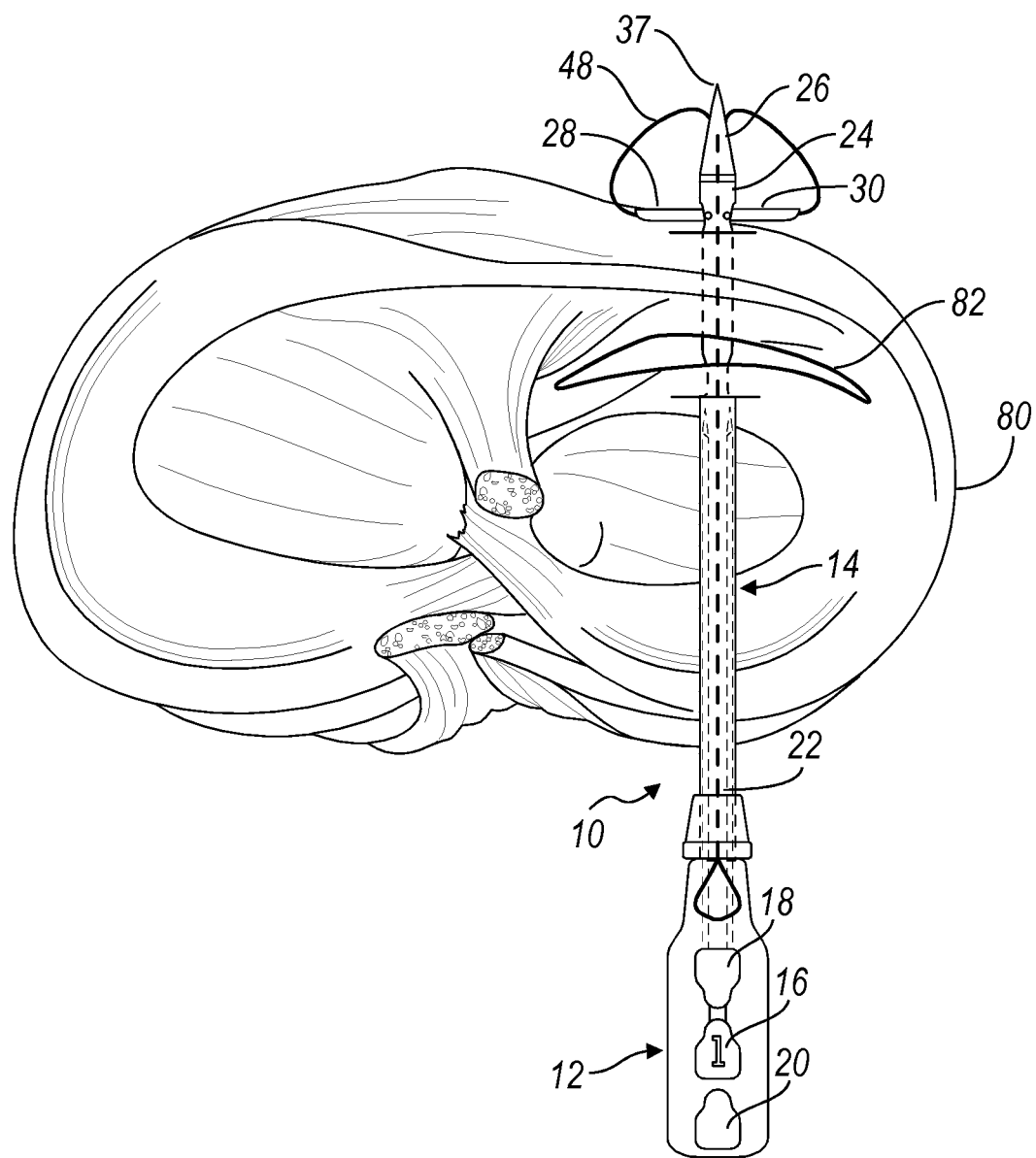
FIG. 7 illustrates the device inserted through the tear of the meniscus with the first and the second wings in the extended position.
Figure 8:
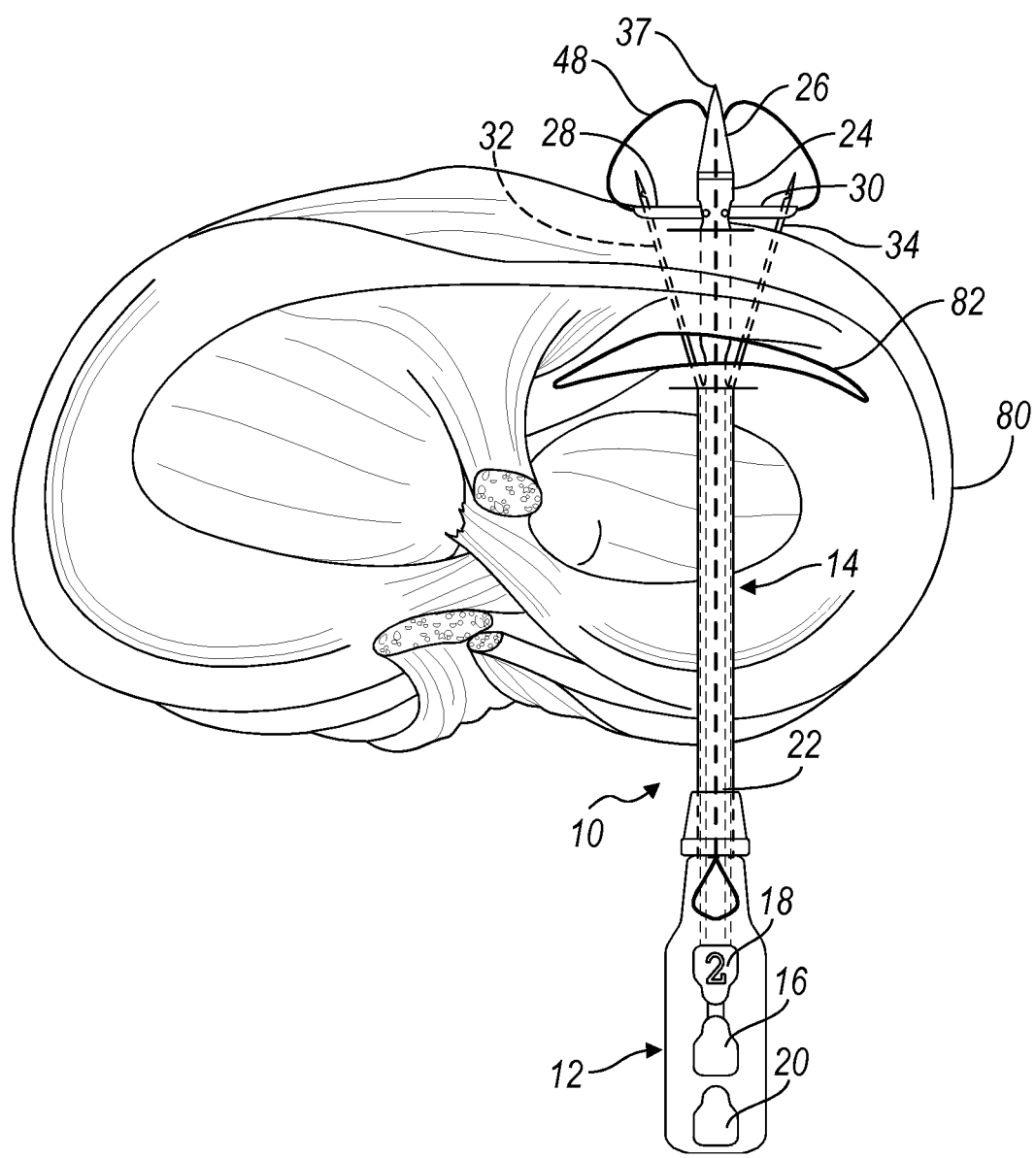
FIG. 8 illustrates the device inserted through the tear of the meniscus with the first and the second needles in the extended position.

As illustrated in FIG. 7, after the distal end 24 of the device 10 is inserted through the tear 82 and the meniscus 80, the first button 16 is pressed to move the first and the second wings 28 and 30 to the extended position. With reference to FIG. 8, the first and the second needles 32 and 34 are moved to the extended position by pressing the second button 18. The device is positioned such that as the first and the second needles 32 and 34 move to the extended position they form two holes in the meniscus 80 through the tear 82, which is in addition to a hole created by the tip 26 of the device 10.

Figure 9:
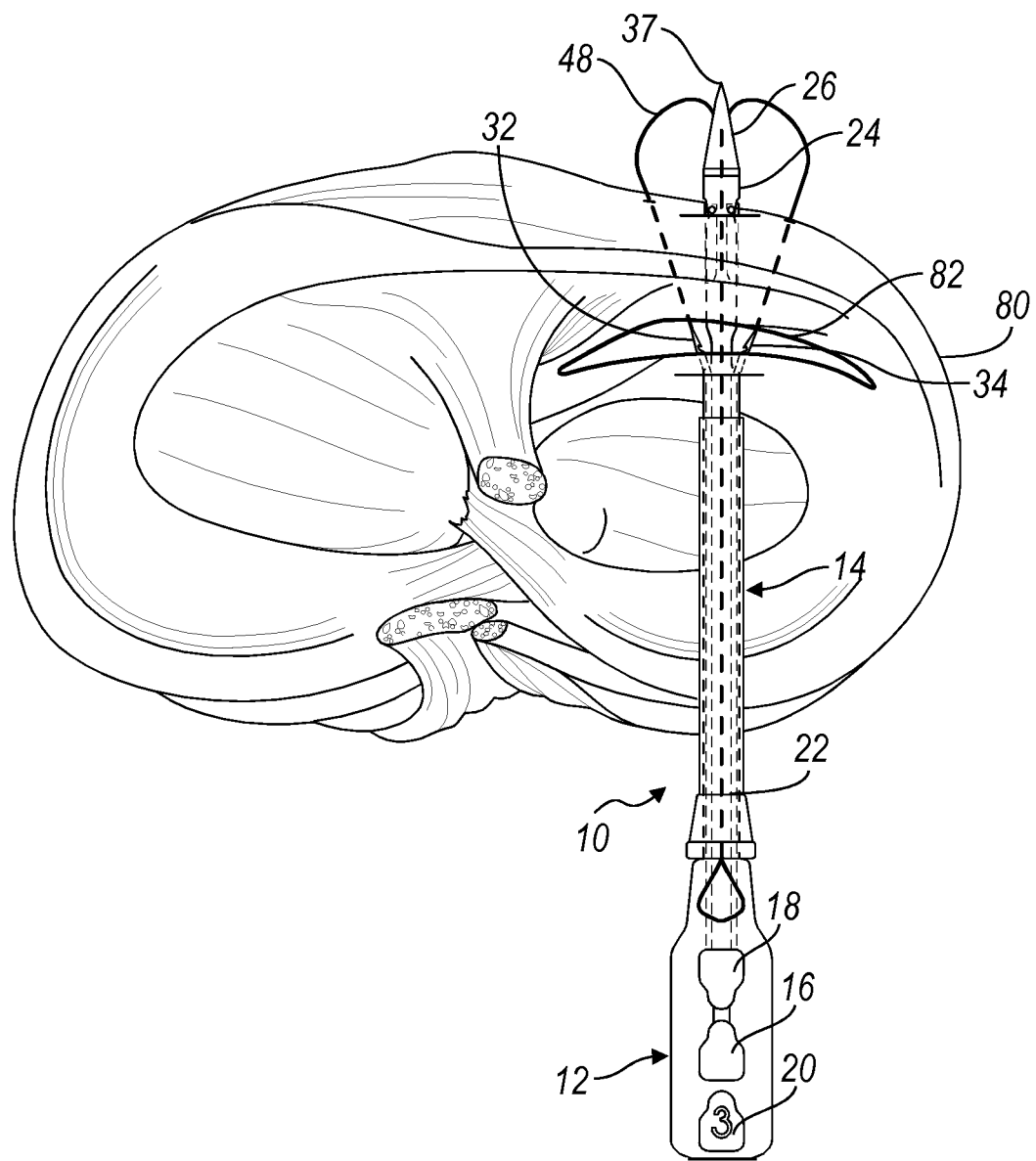
FIG. 9 illustrates the device inserted through the tear of the meniscus with the wings and the needles in their respective retracted positions.
Figure 10:
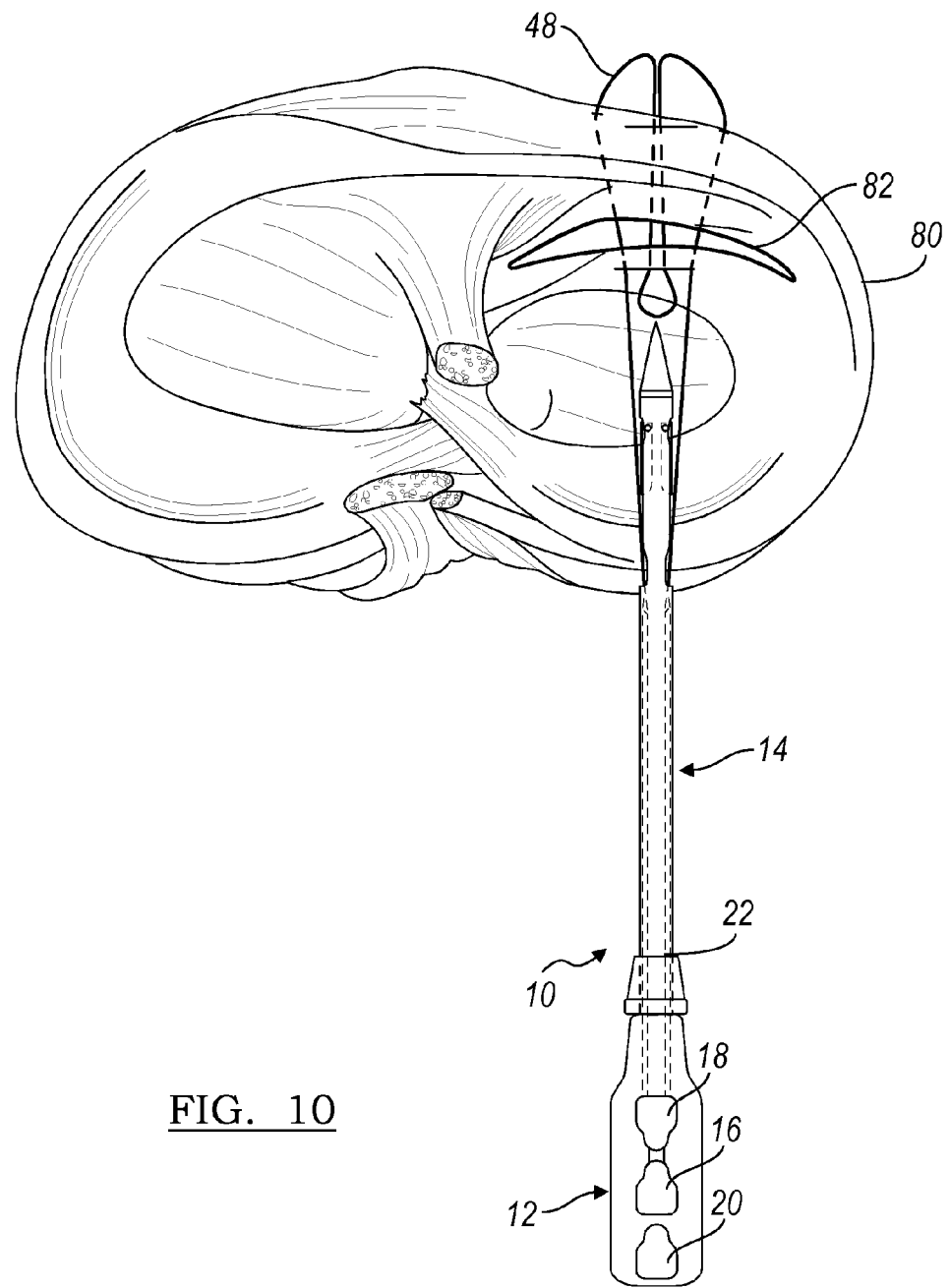
FIG. 10 illustrates the device being withdrawn from the meniscus.

With reference to FIGS. 9 and 10, the first and the second needles 32 and 34 automatically return to the retracted position from the extended position and the first and the second wings 28 and 30 return to the retracted position by pressing the third button 20. As the first and the second needles 32 and 34 retract, they engage the suture 48 by way of the retention surfaces 44 and 46 and pull the suture 48 through the tear 82 by way of the holes created by the needles. Withdrawing the device 10 from within the tear 82 and the meniscus 80 further pulls the suture 48 through the tear 82 and causes the loop 54 of the suture to be withdrawn from within the distal end 24. With additional reference to FIGS. 11 and 12, tension is applied to the first end 50 and the second end 52 of the suture 48 to close the tear 82. The suture 48 can be tied into a knot to secure the suture 48 in place. The hole remaining in the meniscus 80 created by the tip 26 can be used for a variety of different purposes. For example, the hole can receive a meniscal conduit for directing a variety of different biologics, such as nutrients, to the meniscus 80.

Figure 13:
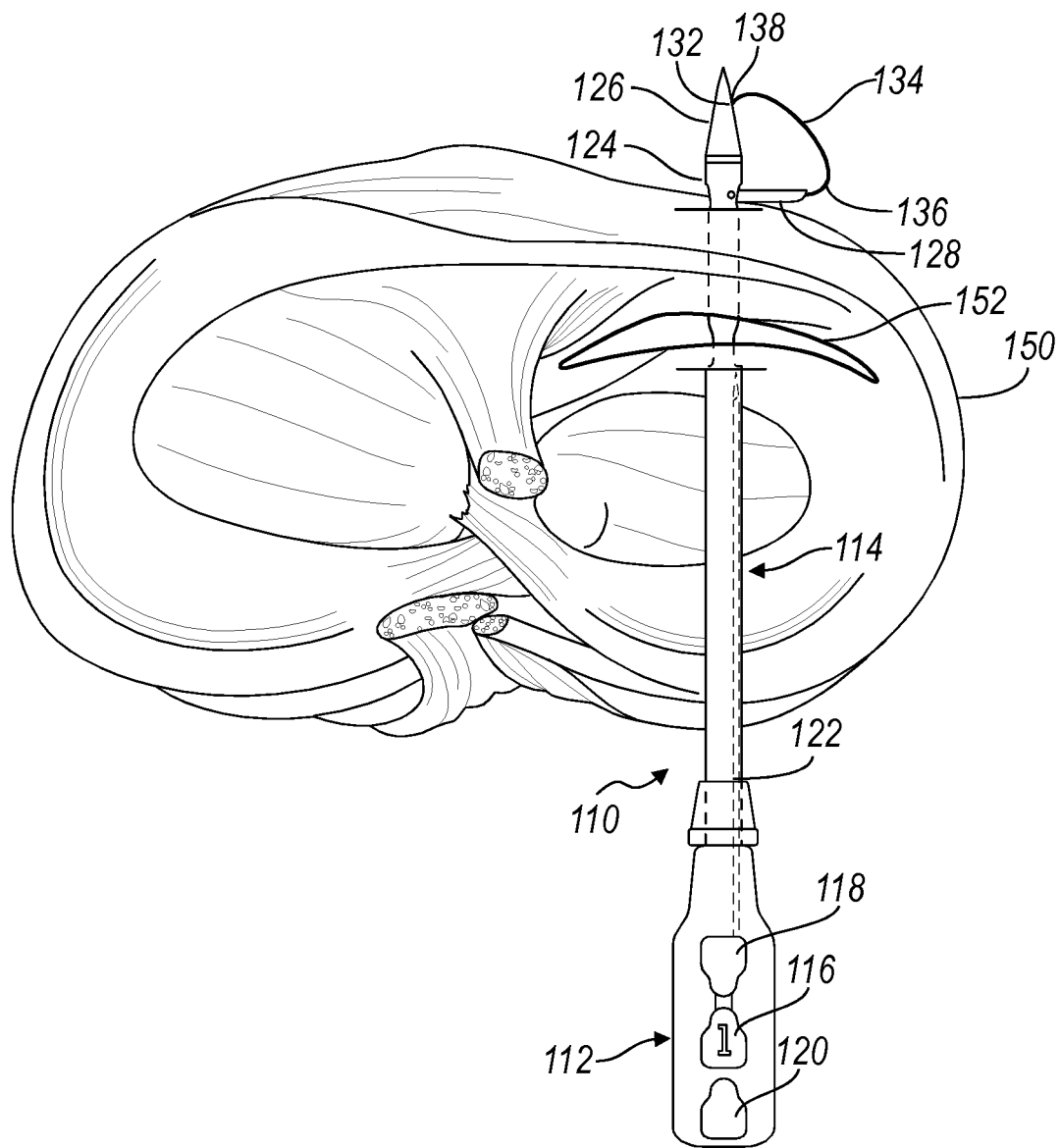
FIG. 13 is a top view of another device according to the present teachings and a superior view of a meniscus having a tear, the device is inserted through the tear in order to insert a suture through the tear.
Figure 14:
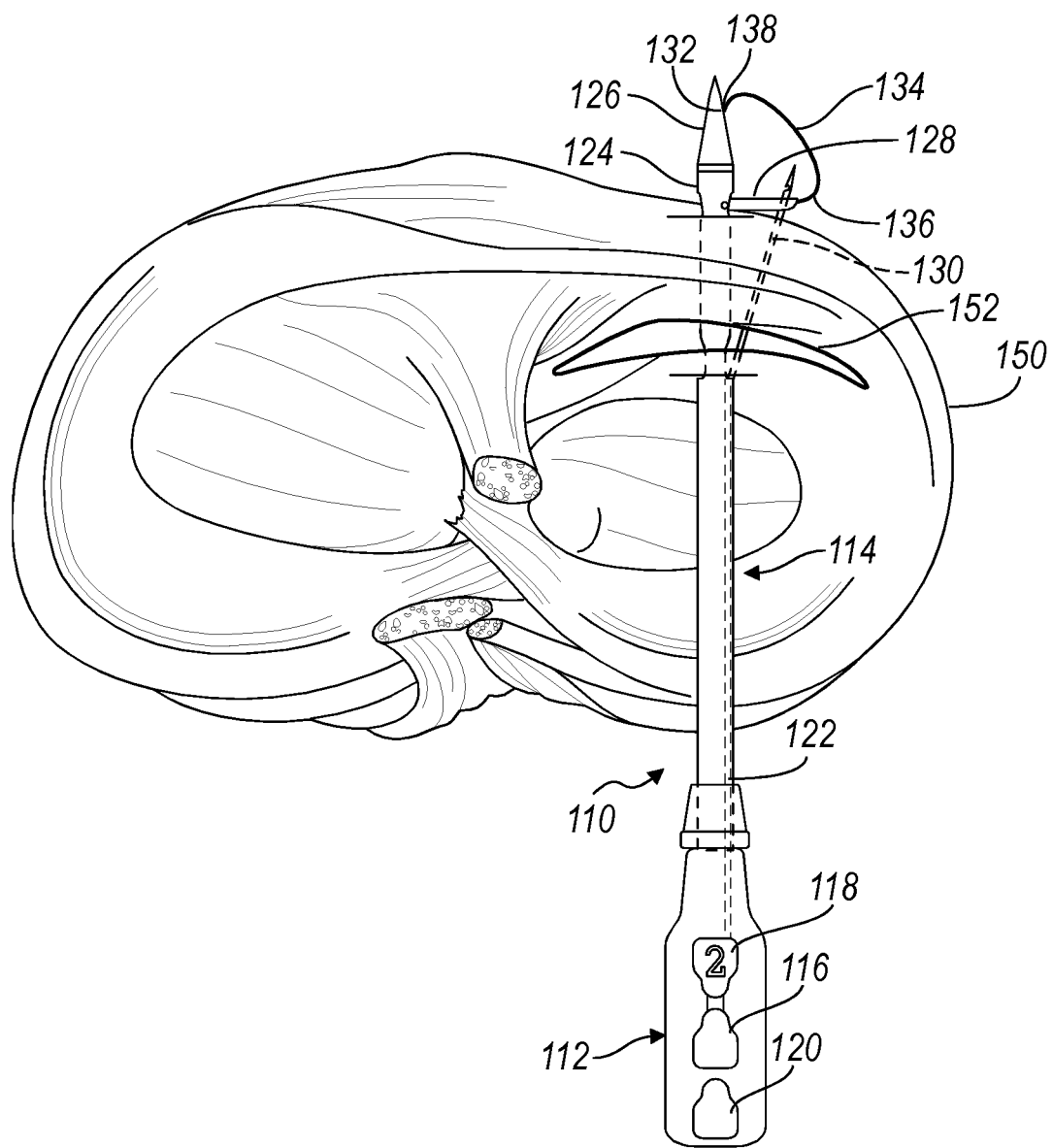
FIG. 14 illustrates the device of FIG. 13 having a single wing and a single needle both in an extended position.
Figure 15:
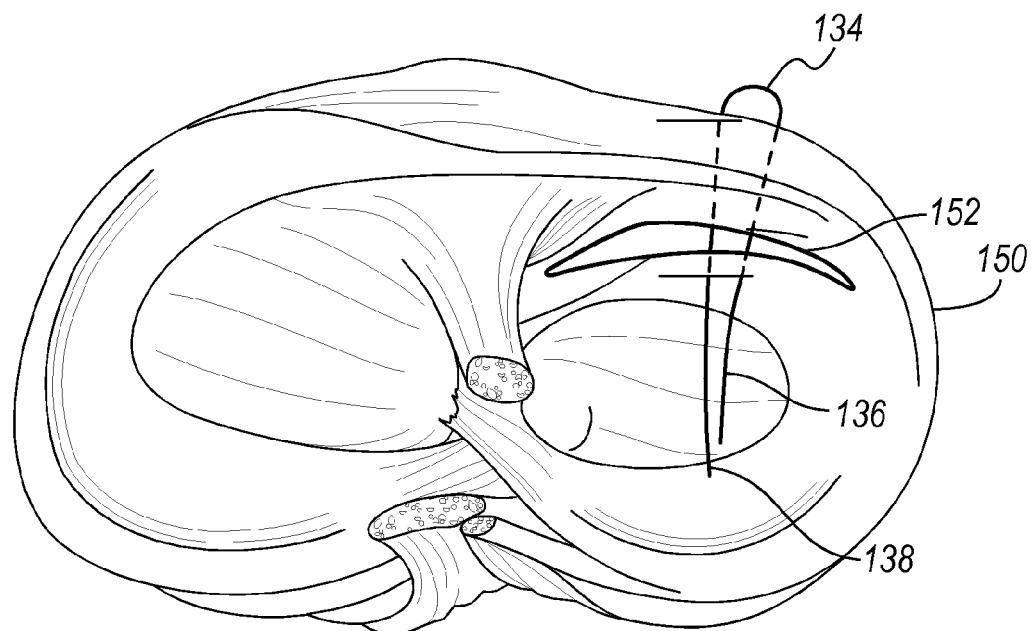
FIG. 15 illustrates the suture inserted through the tear.

With additional reference to FIGS. 13-15, another suture device according to the present teachings is illustrated at reference numeral 110. The device 110 includes a main body 112 and an extended or elongated shaft portion 114 that extends from the main body 112. The main body 112 includes at least one button, switch, or any other device suitable for operating the device 110. As illustrated, the device 110 includes a first button 116, a second button 118, and a third button 120. The device 110 can include any suitable number of buttons for operating the device 110.

The extended shaft portion 114 includes a proximal end 122 and a distal end 124. The proximal end 122 is mounted to the main body 112. The distal end 124 is opposite to the proximal end 122. The distal end 124 includes a pointed conical tip 126, a single suture support illustrated as a single retractable wing 128, and a single suture capturing device illustrated as a single needle 130. The pointed conical tip 126 is designed to pierce tissue. The pointed conical tip 126 includes or defines an opening 132. The opening 132 can be located at any suitable location on the tip 126.

The retractable wing 128 can include a suture guide and a needle opening. The suture guide can take the form of any suitable device for guiding a suture from the extended shaft portion 114 around the wing 128 and to the tip 126. For example, the suture guide can take the form of a recess, indentation, or c-channel formed in the wing 128, such as the recess 40 of FIG. 2A. The needle opening is an opening in the wing 128 that extends completely through the wing 128 and is sized to receive the needle 130.

The wing 128 is movable between a retracted position in which the wing 128 does not extend from the distal end 124 and an extended position (FIG. 13) in which the wing 128 does extend from the distal end 124. The wing 128 is movable to the extended position by actuating the first button 116. The wing 128 is movable to the retracted position by actuating the third button 120.

The needle 130 can be any device capable of penetrating biological matter, such as meniscal tissue. The needle 130 includes a retention surface. The retention surface can be any suitable surface or device for retaining and/or capturing a suture. For example, the retention surface can be a hook or notch formed within the needle 130, such as is illustrated at reference number 44 of FIG. 3A.

The needle 130 is positioned at a side portion of the distal end 124. The needle 130 is aligned with the wing 128. The needle 130 is movable between a retracted position (FIG. 13) and an extended shaft position (FIG. 14). In the retracted position, the needle 130 does not protrude from the extended shaft portion 114. In the extended position, the needle 130 protrudes from the extended shaft portion 114 and extends through the needle opening of the wing 128. The needle 130 can be moved from the retracted position to the extended position by pressing the second button 118. The needle 130 automatically returns to the retracted position after reaching the extended position.

The distal end 124 can receive any suitable fastening device for use in various surgical procedures, such as repairing a meniscal tear. The fastening device is illustrated as a suture 134. When in use, the suture 134 is mounted to the distal end 124 such that a first end 136 of the suture 134 is mounted to, or proximate to, the wing 128 and a second end 138 extends through the opening 132 of the tip 126 and is mounted within the distal end 124.

FIGS. 13-15 illustrate use of the device 110 to repair a meniscus 150 having a tear 152. To close the tear 152, the device 110 is inserted through the meniscus 150 and the tear 152, as illustrated in FIG. 13, such that the distal end 124, and the wing 128 in particular, pass entirely through the meniscus 150. The pointed tip 126 permits the device 110 to pierce the tough meniscus 150. The device 110 is inserted through the meniscus 150 with the wing 128 in the retracted position.

After the device 110 is inserted through the meniscus 150, the first button 116 is pressed to move the wing 128 to the extended position, as illustrated in FIG. 13. With the wing 128 in the extended position, the second button 118 is pressed to move the needle 130 to the extended position, as illustrated in FIG. 14. As the needle 130 moves to the extended position, the needle 130 extends through the tear 152 to create a hole in the tear 152. Thus, the device 110 creates only two holes through the tear 152, the first hole is created by the pointed tip 126 and the second hole is created by the needle 130.

After reaching the extended position, the needle 130 returns to the retracted position. As the needle 130 returns to the retracted position, the retention surface of the needle 130 captures the suture 134 and pulls the suture 134 back through the meniscus 150 and the tear 152. After the needle 130 captures the suture 134, the wing 128 is retracted by pressing the third button 120. As the device 110 is withdrawn back through the tear and out of the meniscus 150, the first end 136 of the suture is pulled through the hole formed by the needle 130 and the second end 138 of the suture 134 is pulled through the hole formed by the tip 126, as illustrated in FIG. 15. The suture 134 can then be tensioned and secured, such as by throwing a knot, to close the tear 152.

Figure 16:
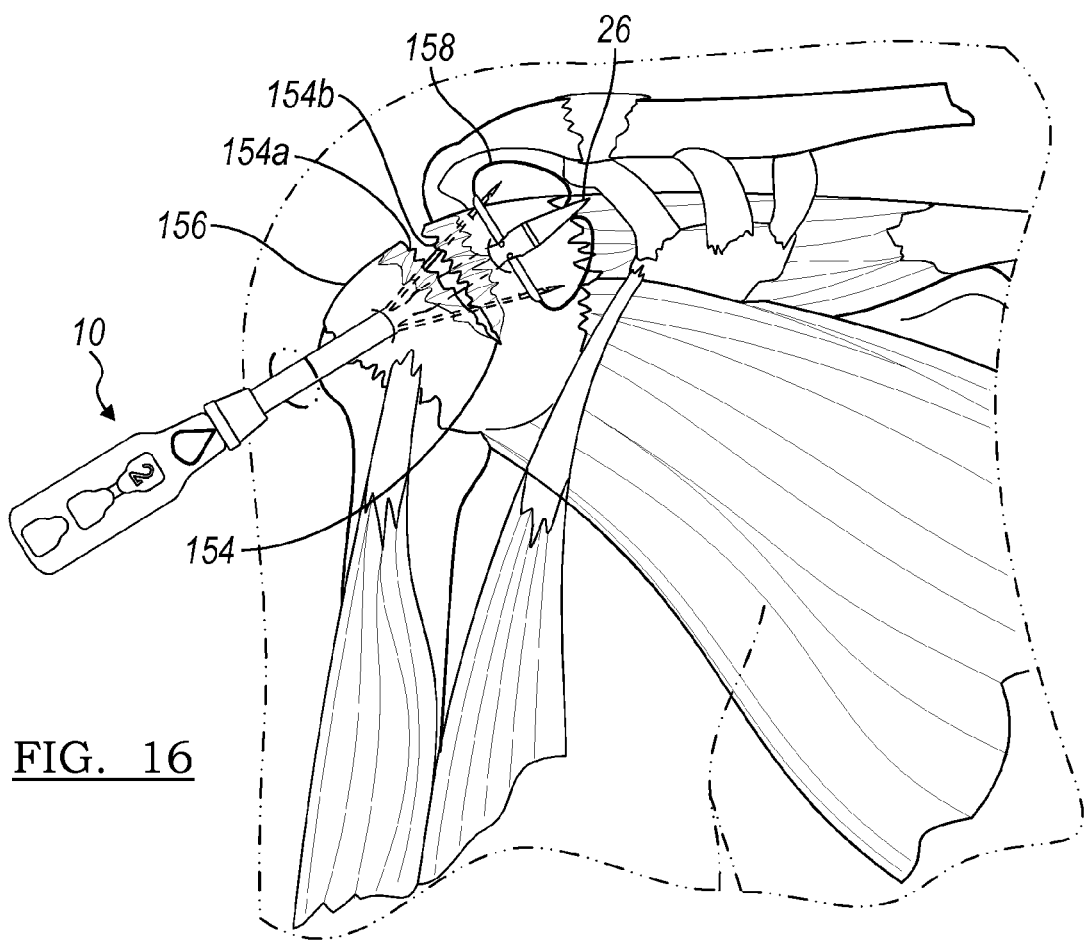
FIG. 16 illustrates use of the device of FIG. 1 to repair a torn rotator cuff.

With additional reference to FIG. 16, the device 10 can also be used to close and repair a tear 154 in a rotator cuff 156. The device 10 can be used to repair most any type of rotator cuff tear, including a margin convergence tear and the tears described in United States Publication No. 2006/0029633 filed on Aug. 3, 2004 and assigned to Biomet Sports Medicine, LLC of Warsaw, Ind., which is incorporated herein by reference. To repair the torn rotator cuff 156 the device 10 is used in substantially the same way described above to repair the tear 82 of the meniscus 80 using the suture 48. Therefore, the above described method for repairing tear 82 can also be used to repair the tear 154 in the rotator cuff 156 using a suture 158. For example, the device 10 pierces the rotator cuff 156 with the tip 26 such that the device 10 is transverse to the tear 154 and extends through both a first side of the tear 154a and a second side of the tear 154b. Further, the device 110 can also be used to repair the rotator cuff 156.

Figure 11:
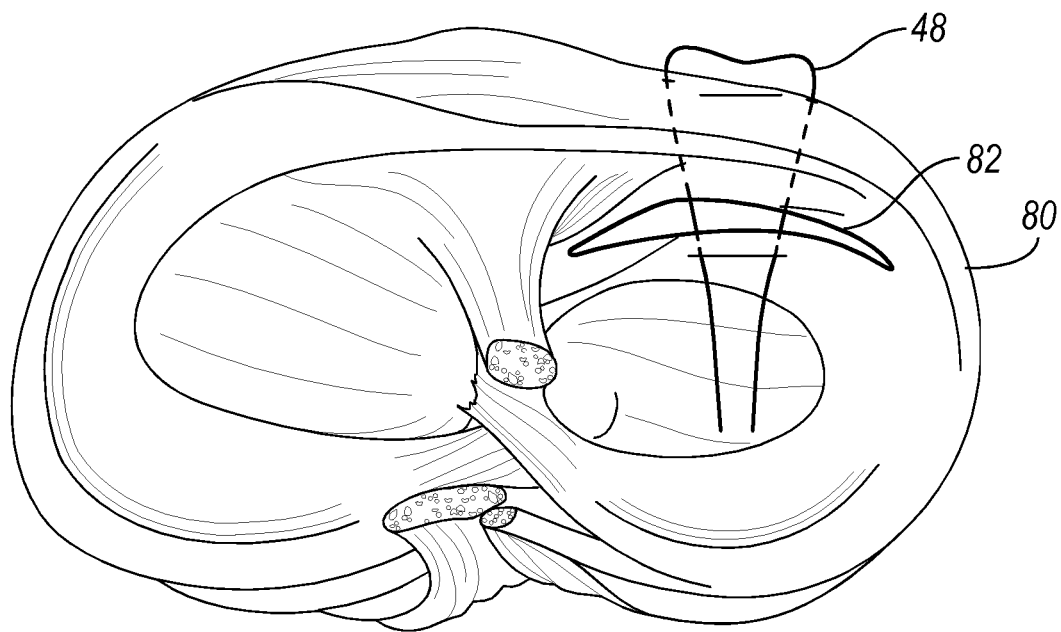
FIG. 11 illustrates the meniscus with a suture through the tear, the suture implanted using the device.
Figure 12:
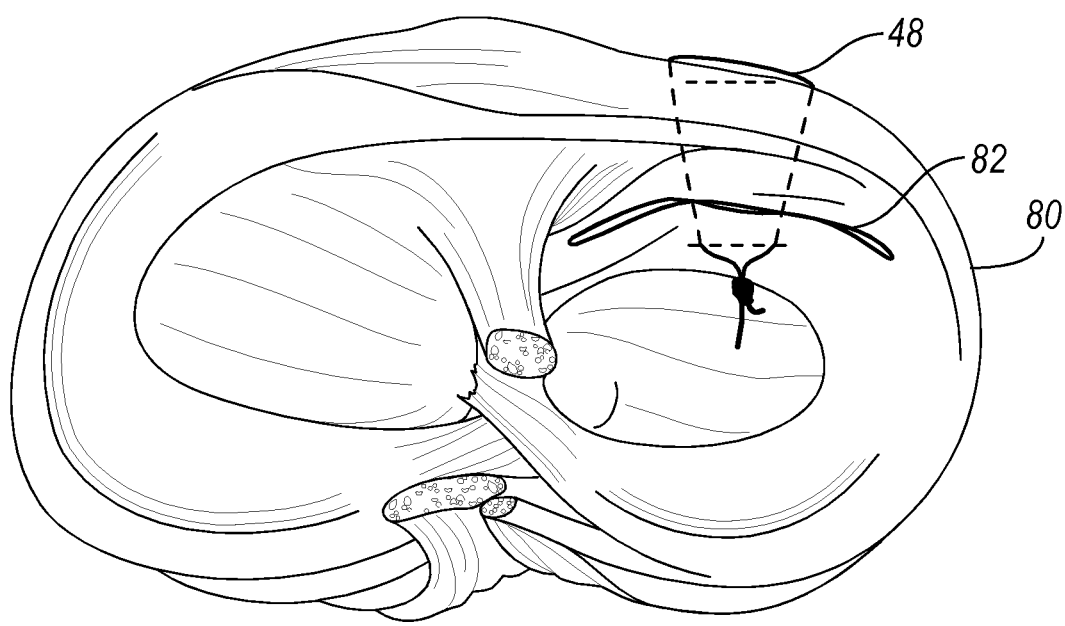
FIG. 12 illustrates the suture tensioned and knotted to secure the tear in a closed position.
Figure 17:
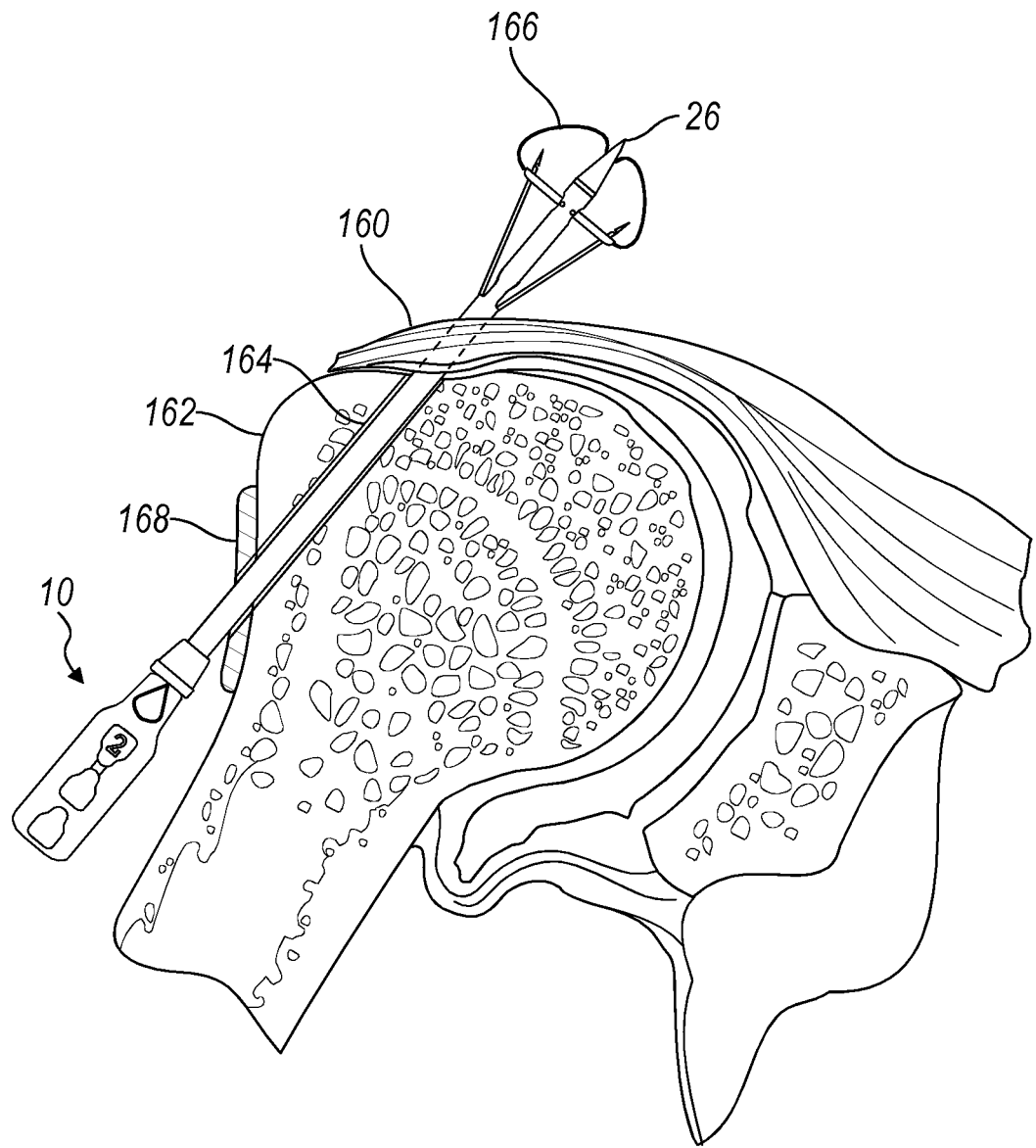
FIG. 17 illustrates use of the device of FIG. 1 to repair a separated rotator cuff.

With reference to FIG. 17, the device 10 can also be used to repair a rotator cuff 160 that has separated from a humerus bone 162. Most any type of rotator cuff separation can be repaired using the device 10, such as the separations described in U.S. Pat. No. 6,514,274 filed on Feb. 4, 2003 and assigned to Biomet Sports Medicine, LLC of Warsaw, Ind., which is incorporated herein by reference. As illustrated, the device 10 can be inserted through a bone hole 164 in the humerus 162 to pierce the rotator cuff 160 using the pointed tip 26 of the device 10. The bone hole 164 can be formed using any suitable device, including the device 10. The tip 26 is a bone piercing tip that can be driven through the humerus bone 162. After the device 10 has pierced the rotator cuff 160, it can be used to insert a suture 166 through the rotator cuff 160 in the same manner described above for inserting the suture 48 through the meniscus 80, as illustrated in FIG. 11. Therefore, the above method for threading the suture 48 through the meniscus 80 can also be used to thread suture 166 through rotator cuff 160. After the suture 166 is threaded through rotator cuff 160, the suture 166 can be secured to the humerus bone 162 using in any suitable manner, such as with a bone plate 168. One skilled in the art will appreciate that the device 10 can be inserted in the opposite direction whereby it pierces the rotator cuff 160 prior to extending through the humerus bone 162. Further, the device 110 can also be used to repair the rotator cuff 160.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A device for implanting a suture, comprising:
   a graspable main body;
   an elongated shaft that extends from said main body, said elongated shaft having a distal end that includes a pointed tissue piercing tip;
   a first suture support mounted to said distal end, said first suture support defining a first opening, said first suture support is movable between a retracted position in which said first suture support does not extend from said distal end and an extended position in which said first suture support does extend from said distal end; and
   a first suture capturing device mounted to said distal end and aligned with said first suture support, said first suture capturing device movable between a retracted position in which said first suture capturing device does not extend from said distal end and an extended position in which said first suturing capturing device extends from said distal end, said first suture capturing device extends within said first opening of said first suture support when in the extended position;
   wherein the suture extends from said first suture support to said tip and extends into said main body through a second opening in said tip; and
   wherein said second opening in said tip comprises a first through hole, a second through hole, and a slot extending between said first through hole and said second through hole, the suture extends through the first through hole, the second through hole, and the slot.

2. The device of claim 1, wherein said first suture support comprises a wing that includes a recess to direct the suture across the wing.

3. The device of claim 2, wherein said device consists of only a single suture support.

4. The device of claim 1, wherein said first suture capturing device comprises a needle having a retention notch proximate to a tip of said needle.

5. The device of claim 4, wherein said device consist of only a single needle.

6. The device of claim 1, further comprising a second suture support mounted to said distal end at a position opposite to said first suture support; and
   a second suture capturing device mounted to said distal end at a position opposite to said first suture capturing device.

7. The device of claim 6, wherein the first suture capturing device and the second suture capturing device move from the retracted position to the extended position in a similar direction.

8. The device of claim 1, wherein the pointed tissue piercing tip is a pointed conical tip sharpened and configured to pierce tissue, wherein said first through hole, said second through hole, and said slot are defined in the conical tip.

9. A device for implanting a suture, comprising:
   a graspable main body;
   an elongated shaft that extends from said main body, said elongated shaft having a proximal end attached to the main body and a distal end;
   a pointed conical tip extending from the distal end configured to facilitate piercing tissue;
   a first suture support mounted to said distal end, said first suture support movable between a retracted position and an extended position from said distal end, said first suture support defining a first opening;

a second suture support mounted to said distal end, said second suture support movable between a retracted position and an extended position from said distal end, said second suture support defining a second opening;

a first suture capturing needle movably positioned at said distal end, said first suture capturing needle movable between a retracted position in which said first suture capturing needle does not extend from said distal end and an extended position in which said first suture capturing needle extends from said distal end, said first suture capturing needle extending within said first opening of said first suture support when in an extended position; and a second suture capturing needle movably positioned at said distal end, said second suture capturing needle movable between a retracted position in which said second suture capturing needle does not extend from said distal end and an extended position in which said second suture capturing needle extends from said distal end, said second suture capturing needle extending within said second opening of said second suture support when in an extended position;

wherein the suture extends from the first suture support to said tip and to said second suture support; and wherein said conical tip defines a first through hole, a second through hole, and a slot extending between the first through hole and said second through hole, the suture positioned within the first and second holes and the slot being configured to allow the suture to exit from said conical tip.

10. The device of claim 9, wherein the first suture support comprises a wing that includes a suture guide configured to position the suture over said first opening.

11. The device of claim 10, wherein said first suture capturing needle includes a retention notch proximate to a tip of said needle and configured to capture the suture positioned over said first opening as said first suture capturing needle extends within said first opening.

12. The device of claim 9, wherein the first suture support and the second suture support move from the retracted position to the extended position in a similar direction.

13. The device of claim 9, wherein the first suture capturing needle and the second suture capturing needle move from the retracted position to the extended position in a similar direction.

14. A device for implanting a suture, comprising:
an elongated shaft that extends from a proximal end to a distal end;
a pointed conical tip configured to pierce tissue extending from said distal end;
a first suture support pivotably mounted to said distal end, said first suture support having a first end and a second end, said first end pivotably coupled to said elongated shaft, said second end having a suture guide, said first suture support pivotable between a retracted position in which said first suture support does not extend from said distal end and an extended position in which said first suture support does extend from said distal end; and a first suture capturing device slidably mounted relative to said distal end, said first suture capturing device slidable between a retracted position in which said first suture capturing device does not extend from said distal end and an extended position in which said first suture capturing device extends from said distal end to said first suture support;

wherein the suture extends from said suture guide of said first suture support to said conical tip and extends into said elongated shaft through an opening in said conical tip; and wherein said opening in said conical tip includes a first through hole, a second through hole, and a slot extending between said first through hole and said second through hole to allow the suture to extend into said elongated shaft and exit said elongated shaft, the suture extends through the first through hole, the second through hole, and the slot.

15. The device of claim 14, wherein said first suture support defines a first opening at said second end adjacent said suture guide and said first suture capturing device in said extended position extends within said first opening to engage the suture.

16. The device of claim 14, further comprising:
a second suture support pivotably mounted to said distal end, said second suture support having a first end and a second end, said first end pivotably coupled to said elongated shaft, said second end having a suture guide, said second suture support pivotable between a retracted position in which said second suture support does not extend from said distal end and an extended position in which said second suture support does extend from said distal end; and a second suture capturing device slidably mounted relative to said distal end, said second suture capturing device slidable between a retracted position in which said second suture capturing device does not extend from said distal end and an extended position in which said second suture capturing device extends from said distal end to said second suture support.

17. The device of claim 16, wherein said first suture support and said second suture support pivot in substantially the same direction from the retracted position to the extended position.

* * * * *